(12) United States Patent
Zhang et al.

(10) Patent No.: US 10,961,510 B2
(45) Date of Patent: *Mar. 30, 2021

(54) EXOSOME ACTIVE FORMULATION FOR PROMOTING ENDOTHELIAL CELL ANGIOGENESIS, AND PREPARATION METHOD AND APPLICATION

(71) Applicant: INSTITUTE OF MICROCIRCULATION of the CHINESE ACADEMY OF MEDICAL SCIENES & PEKING UNION MEDICAL COLLEGE, Beijing (CN)

(72) Inventors: Honggang Zhang, Beijing (CN); Qiuju Zhang, Beijing (CN); Bingwei Li, Beijing (CN); Ruijuan Xiu, Beijing (CN)

(73) Assignee: INSTITUTE OF MICROCIRCULATION (OF THE CHINESE ACADEMY OF MEDICAL SCIENCES & PEKING UNION MEDICAL COLLEGE), Beijing (CN)

(*) Notice: Subject to any disclaimer, the term of this patent is extended or adjusted under 35 U.S.C. 154(b) by 0 days.

This patent is subject to a terminal disclaimer.

(21) Appl. No.: 16/956,575

(22) PCT Filed: Apr. 29, 2019

(86) PCT No.: PCT/CN2019/085071
§ 371 (c)(1),
(2) Date: Jun. 20, 2020

(87) PCT Pub. No.: WO2019/210833
PCT Pub. Date: Jul. 11, 2019

(65) Prior Publication Data
US 2021/0009948 A1 Jan. 14, 2021

(30) Foreign Application Priority Data
May 3, 2018 (CN) .......................... 201810413685.0

(51) Int. Cl.
C12N 5/071 (2010.01)
A61K 35/44 (2015.01)
A61P 9/14 (2006.01)

(52) U.S. Cl.
CPC ............ *C12N 5/069* (2013.01); *A61K 35/44* (2013.01); *A61P 9/14* (2018.01); *C12N 2501/165* (2013.01); *C12N 2501/998* (2013.01); *C12N 2501/999* (2013.01)

(58) Field of Classification Search
None
See application file for complete search history.

(56) References Cited

U.S. PATENT DOCUMENTS

2016/0108368 A1    4/2016  Larocca
2020/0316134 A1*  10/2020  Ricordi ..................... A61P 3/10

FOREIGN PATENT DOCUMENTS

| CN | 107937342 A |   | 4/2018 |           |
|----|-------------|---|--------|-----------|
| CN | 108753682   | * | 11/2018 | ............. A61K 35/44 |
| CN | 108753682 A |   | 11/2018 |           |

OTHER PUBLICATIONS

Li etal, Journal of Diabetes and Its Complications, 2016, vol. 30, pp. 986-992 (Year: 2016).*
Thery et al, Current Protocols in Cell Biology, 2006, vol. 30, Issue 1, pp. 3.22.1-3.22.29 (Year: 2006).*
Zhang, Yi-Zhe, Fan Liu, Chang-Geng Song, Xiu-Li Cao, Yu-Fei Zhang, Hai-Ning Wu, Chen-Jun Gu, Yong-Qiang Li, Qi-Jun Zheng, Min-Hua Zheng, Hua Ha "Exosomes Derived from Human Umbilical Vein Endothelial Cells Promote geural Stem Cell Expansion While Maintain Their Sternness in Culture" Biochemical and Biophysical Research Communications, Nov. 15, 2015, vol. 495, Nr.:1, pp. 892-897, XP055648816, Communications, Nov. 15, 2015 Doi: https://dx.doi.org/10.1016/j.bbrc.2017.11.092.

* cited by examiner

*Primary Examiner* — Allison M Fox
(74) *Attorney, Agent, or Firm* — Craft Chu PLLC; Andrew W. Chu

(57) ABSTRACT

An exosome active formulation for promoting endothelial cell angiogenesis, and a preparation method and use thereof include the following steps: isolating primary umbilical vein endothelial cells and performing cell culture and passage; adding anisodamine to a culture medium of the subcultured endothelial cells to treat the endothelial cells, and then replacing the culture medium with a new endothelial cell culture medium to continue the culture of the endothelial cells; extracting exosomes from the endothelial cell culture medium obtained after the endothelial cells are cultivated; and identifying the exosomes. The exosome active formulation for promoting endothelial cell angiogenesis prepared by the preparation method and its use in the manufacture of a medicament for treating microvascular injury, microcirculation dysfunction and cardio-cerebral infarction.

6 Claims, 3 Drawing Sheets

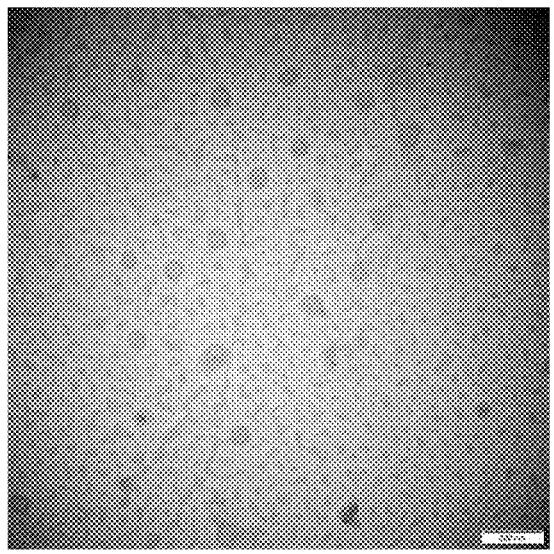
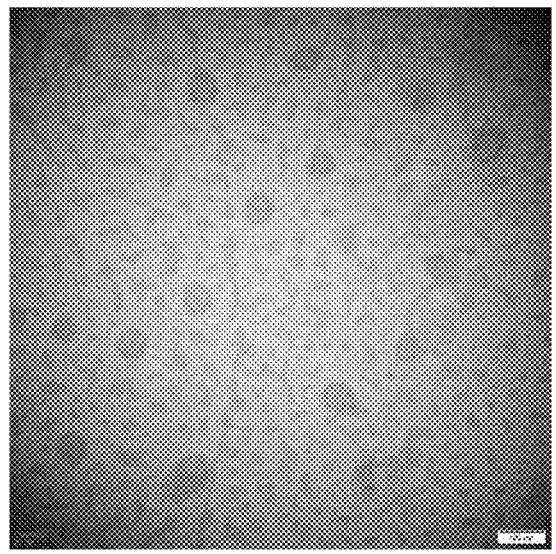
Fig.1A Fig.1B
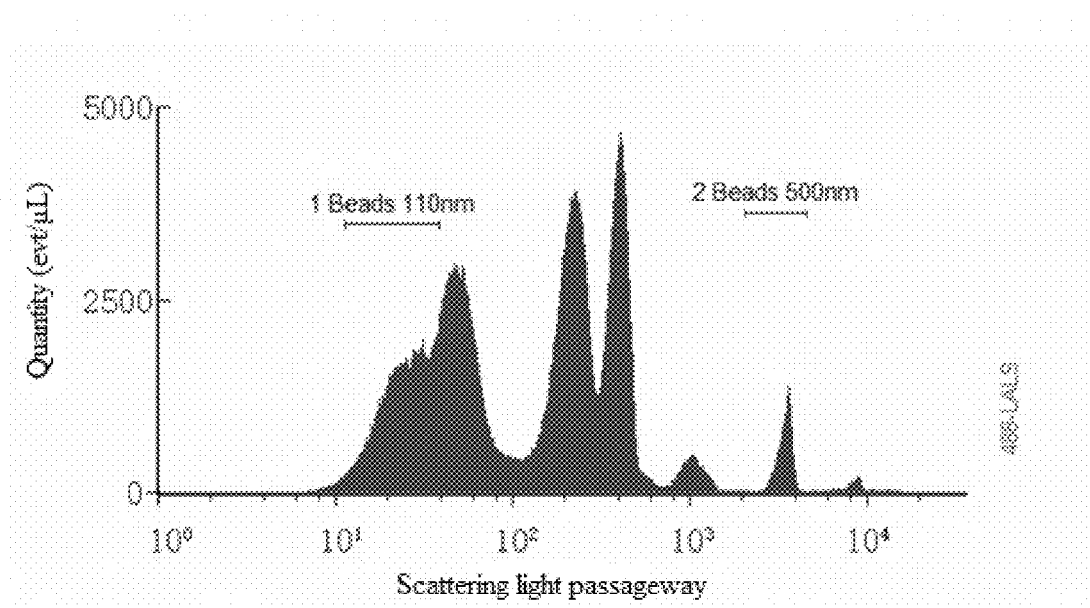
Fig. 2A

EXOSOME ACTIVE FORMULATION FOR PROMOTING ENDOTHELIAL CELL ANGIOGENESIS, AND PREPARATION METHOD AND APPLICATION

CROSS-REFERENCE TO RELATED APPLICATIONS

See Application Data Sheet.

STATEMENT REGARDING FEDERALLY SPONSORED RESEARCH OR DEVELOPMENT

Not applicable.

THE NAMES OF PARTIES TO A JOINT RESEARCH AGREEMENT

Not applicable.

INCORPORATION-BY-REFERENCE OF MATERIAL SUBMITTED ON A COMPACT DISC OR AS A TEXT FILE VIA THE OFFICE ELECTRONIC FILING SYSTEM (EFS-WEB)

Not applicable.

STATEMENT REGARDING PRIOR DISCLOSURES BY THE INVENTOR OR A JOINT INVENTOR

Not applicable.

BACKGROUND OF THE INVENTION

1. Field of the Invention

This disclosure relates to the field of biological medicine, and particularly relates to an exosome active formulation for promoting endothelial cell angiogenesis, and a preparation method and use thereof.

2. Description of Related Art Including Information Disclosed Under 37 CFR 1.97 and 37 CFR 1.98

Microcirculation is the blood circulation in the capillaries between arterioles and venules, which is the most basic structural and functional unit in the circulation system, and it includes the body fluid circulation in the arterioles, venules, capillary lymphatic vessels and tissue conduits. For each organ and each tissue cell of a human body, the supply of oxygen and nourishments, transfer of energy and exchange of information as well as the discharge of carbon dioxide and metabolization of wastes are performed through the microcirculation. Once the microcirculation of a human body is dysfunctional, its corresponding tissue system or visceral organ will be affected so that their function cannot be properly perform, and thus it will easily result in aging, immune function dysfunction and disease occurrence in the human body.

Microcirculation dysfunctions are important pathophysiological basis for the occurrence and development of diseases. The microcirculation function is the primary prerequisite for ensuring the normal function of the human organs. Medical science has demonstrated that the dysfunction of microcirculation causes many people in a sub-health status, and major chronic diseases, such as tumors, hypertension, diabetes and many cardio-cerebrovascular diseases, and the like, are associated with microcirculation dysfunctions. Therefore, the microcirculation function is also an important indicator of whether a human body is healthy.

In view of this, the improvement of microcirculation can enhance the therapeutic efficacy for treatment of diseases from a viewpoint of the whole organism, and can correct microcirculation dysfunctions through the improvement of microcirculation so as to achieve the purpose of aiding the treatment of diseases. A microcirculation dysfunction therapy can quickly improve the blood-supply and oxygen-supply functions of the systemic tissues, reduce blood fat and blood viscosity, increase metabolism, boost the immunity of the organism, and has a significant therapeutic efficacy for various diseases such as cardio-cerebrovascular diseases, hyperlipidaemia, and the like. The basic principle for treating myocardial infarction and stroke lies in the reconstruction of collateral pathways after infarct, while the reconstruction of collaterals mainly depends on angiogenesis.

With the deepening of research on cellar exosomes, the exosomal drug formulations increasingly become a hotspot in research on the treatment of diseases. An exosome is a transportation vesicle that is secreted and released into the extracellular environment by a living cell, and has a size of 60-100 nm. The exosome can deliver chemical drugs, proteins as well as peptide ligands, gene drugs and other drugs due to its natural material-transporting property, relatively smaller molecular structure and excellent biocompatibility, and thus has a huge potential in the field of drug carriers.

In recent years, an exosome, as a natural intercellular information carrier, has a huge application potential in the field of drug carriers due to its natural material-transporting property, relatively smaller molecular structure and excellent biocompatibility. For the selection of drug carriers, there are two basic principles: protection of a drug contained therein to maintain its activity in an in vivo environment; and release of the inclusion without inducing an immune response of an organism to the drug carrier. Compared to the existing drug carriers (such as an artificial liposome), the exosome has its remarkable advantages. Firstly, the exosome has its own natural inclusions, can be transferred to a receptor cell and functionally changes the receptor cells, meanwhile the surface molecules on the exosomes derived from different sources are different and have certain selectivity to the receptor cells, which is more advantageous in terms of treatment. Secondly, compared to the lower packaging efficiency of a liposome to a hydrotropic substance, which thus is limited in term of the nucleic acid delivery, while an exosome can better affiliate nucleic acid molecules and thus significantly improve the packaging efficiency. Due to a low immunogenicity, an exosome can avoid the interaction with opsonin proteins, antibodies, coagulation factors, and the like, thereby the occurrence of immune responses in the body.

The use of an exosomal drug to improve microcirculation increasingly has advantages, because microcirculation is a tiny blood circulation throughout the organism, and an exosomal drug, via blood circulation, can more easily reach vascular cells to achieve the purpose of treatment. In cardio-cerebrovascular diseases, accompanying the generation of angiogenesis-affecting inflammatory factors such as tumor necrosis factors (TNF-$\alpha$) and the like, it is an important content in the treatment of ischemia that new microvessels can be formed in an environment of inflammatory factors such as TNF-$\alpha$.

BRIEF SUMMARY OF THE INVENTION

The technical problem to be solved by this disclosure is to provide an exosome active formulation for promoting endothelial cell angiogenesis, and a preparation method and use thereof.

The technical solutions for solving the above technical problem of this disclosure are as follows: a preparation method of an exosome active formulation for promoting endothelial cell angiogenesis comprises the following steps:

(1) isolating primary umbilical vein endothelial cells and performing cell culture and passage;

(2) adding anisodamine to a culture medium of the subcultured endothelial cells to treat the endothelial cells, and then replacing the culture medium with a new endothelial cell culture medium to continue the culture of endothelial cells;

(3) extracting exosomes from the endothelial cell culture medium obtained after the endothelial cells are cultivated; and (4) identifying the exosomes.

Further, the subcultured endothelial cells are endothelial cells of passages 3-5.

Further, the endothelial cell culture medium is a basic culture medium with addition of exosome-free fetal calf serum, penicillin, streptomycin and an endothelial growth factor to a final concentration of 0.05 mg/mL, 0.01 mg/mL, 0.01 mg/mL and 0.01 mg/mL, respectively.

Further, in the endothelial cell culture medium with anisodamine added in step (2), the concentration of anisodamine is $1.5\times10\text{-}2\text{-}1.5\times10\text{-}3$ ng/mL, the time for treatment is 3-5 hours after anisodamine is added, and the time for continuing the culture of the endothelial cells after the new endothelial cell culture medium is used is 18-30 hours.

Further, the specific steps for extracting exosomes in the step (3) comprise: collecting the supernatant of the endothelial cell culture medium obtained after the endothelial cells are cultivated in step (2) and centrifuging it at 4° C. and 300 g for 10 minutes, taking the supernatant and centrifuging it at 4° C. and 16500 g for 20 minutes, taking the supernatant and filtering it via a filter membrane with a pore size of 0.2?m, taking the supernatant and centrifuging it at 4° C. and 120000 g for 2 hours, removing the supernatant, and dissolving the precipitates in an 0.01 M PBS buffer solution.

Further, the identification of the exosomes in the step (4) comprises: observing the morphology of the exosomes with a transmission electron microscope, analyzing the particle size of the exosomes and quantifying the exosomal proteins.

Further, this disclosure provides an exosome active formulation for promoting endothelial cell angiogenesis prepared by the above preparation method.

The beneficial effects of this disclosure are that: the exosomes prepared by the preparation method of this disclosure can promote endothelial cell angiogenesis, and the preparation method is simple.

Further, this disclosure provides the use of an exosome active formulation for promoting endothelial cell angiogenesis in the manufacture of a medicament for treating microvascular injury, microcirculation dysfunction and cardiocerebral infarction.

The beneficial effects of utilizing the above further solution are that: the promotion of endothelial cell angiogenesis has an important effect on the improvement of microcirculation, the improvement of microcirculation has a significant therapeutic efficacy on cardio-cerebrovascular diseases, and the exosomal drugs have certain selectivity to the receptor cells and a higher delivery efficiency compared to the conventional drugs.

BRIEF DESCRIPTION OF THE SEVERAL VIEWS OF THE DRAWINGS

FIG. 1A and FIG. 1B are the transmission electron microscope diagrams of exosomes in experiment group N according to this disclosure, wherein the scale in FIG. 1A is 200 nm, and the scale in FIG. 1B is 100 nm.

FIG. 2A and FIG. 2B are graph illustrations of the particle size results of exosomes detected by using a scattered light pathway of an Apogee nano flow cytometry according to this disclosure, with a gating range is 50~110 nm when detection, wherein FIG. 2A is a histogram of the detection results of standard microsphere mixtures having particle sizes of 180 nm, 240 nm, 300 nm, 590 nm, 880 nm and 1300 nm, and FIG. 2B is a histogram of the detection result of an exosome in experiment group N according to this disclosure.

DETAILED DESCRIPTION OF THE INVENTION

Figure 2B:
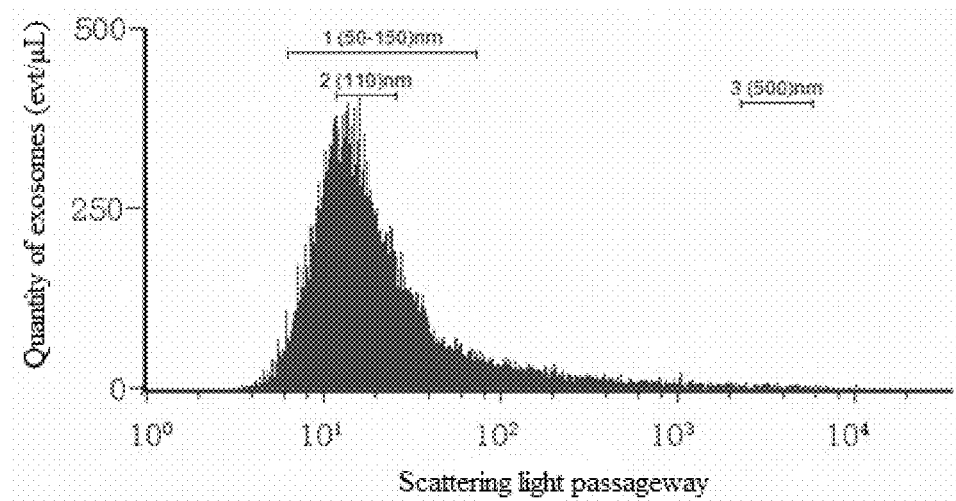

Hereinafter, the principle and features of this disclosure will be described in conjunction with the drawing and embodiments, and the examples are listed only for explaining this disclosure, but not for limiting the scope of this disclosure.

Example 1 Culture and Subculture of Primary Endothelial Cells

The umbilical cords of healthy delivery women were collected, and the primary umbilical vein endothelial cells were isolated via a collagenase digestion method, and primary cell culture was performed. The preparation method of an endothelial cell culture medium was as follows: an exosome-free fetal bovine serum, an endothelial growth factor, penicillin and streptomycin were added to a basic endothelial cell culture medium, wherein the final concentrations of the exosome-free fetal bovine serum, the endothelial growth factor, the penicillin and the streptomycin were 0.05 mg/mL, 0.01 mg/mL, 0.01 mg/mL and 0.01 mg/mL, respectively. The devices for the cell culture were as follows: a culture flask, a culture dish and a culture plate. The conditions for the cell culture were as follows: sterile, 37° C., 5% CO2, saturated humidity, and the culture medium being replaced every other day.

The primary endothelial cells were cultured for 2~3 days for passage. The digestive solution for cell passage comprised 0.25% trypsase and 0.02% EDTA. The cell culture flask was taken out, and the cap was tightened. The cell status and the confluence degree were observed under an inverted microscope, then the subsequent operations were performed in a super-clean workbench. The old culture medium was aspirated, and a small amount of PBS was added for washing twice so as to remove serum from the residual culture medium. PBS was aspirated, and then an appropriate amount of the digestive solution was added, preferably to cover the cell monolayer. The digestive progress was observed under an inverted microscope, and the digestive solution was aspirated after the cells were retracted and rounded to be spherical shape. An appropriate amount of a complete culture medium was added to neutralize the residual digestive solution, which was evenly blown and beaten by a pipette, and the condition after digestion was observed under an inverted microscope. The cells were subcultured in separate flasks with a ratio of 1:2~1:3, and the amount of a complete culture medium was supplemented respectively, and then the caps of the culture flasks were tightened. The cells were evenly spread, and then the caps of the culture flasks were loosened with a half-turn, and subsequently the culture flasks were placed in a CO2 incubator for normal culture.

Example 2 Preparation of Exosomes

The experiments were divided into two groups, the control group C and the experimental group N, respectively. The endothelial cells of passages 3~5 were grown to confluence in a 10 cm culture dish, wherein the endothelial cells were cultivated for 24 hours with a endothelial cell culture medium in the control group; and the endothelial cells were treated for 4 hours by adding $1.5 \times 10^{-2}$-$1.5 \times 10^{-3}$ anisodamine to the culture medium in the experiment group N, the supernatant was aspirated to remove anisodamine, and an endothelial cell culture medium was added to continue the culture for 24 hours.

Anisodamine used in this example was a rac-anisodamine tablet purchased from Hangzhou Minsheng Pharmaceutical Co., Ltd.

Example 3 Extraction and Purification of Exosomes

The supernatant of the final endothelial cell culture medium was collected and centrifuged at 300 g and 4° C. for 10 minutes. Then the supernatant was taken and centrifuged at 16500 g and 4° C. for 20 minutes. Then the supernatant was taken and filtered by a filter membrane with a pore size of 0.2 μm. Then the filtrate was taken and centrifuged at 120000 g and 4° C. for 2 hours. Then the supernatant was removed, and the precipitate was dissolved in 100 μL of a 0.01 M PBS buffer solution to obtain an exosome active formulation for promoting endothelial cell angiogenesis.

Example 4

The morphology of the exosomes was observed by using a transmission electron microscope. The results were shown in FIGS. 1A and 1B, the exosomes obtained in the experimental group were globules having a homogeneous morphology with a diameter of slightly less than 100 nm and having a teacup holder-like structure with a clear membrane, which was a typical transmission electron microscope morphology of exosomes.

The particle size of the exosomes was detected by using the scattering light passageway of an Apogee nano-flow cytometry. The results were showed in FIG. 2A and FIG. 2B. FIG. 2B showed that the resultant exosomes had only one peak in the gating range of 50-110 nm, indicating that the resultant exosomes had a high purity without impurities.

The quantification of exosomal proteins was performed by using a BCA method, and the results were as shown in Table 1. The concentrations of exosomes generated in the experimental group were slightly lower than those in the control group.

Example 5 Angiogenesis Ability of Exosomes from Different Sources

The angiogenesis ability of human umbilical vein endothelial cells (HUVECs) was detected by using a 96-well plate coated with a basement membrane extract (BME). 50 μL of a BME solution was added in each well, which was placed in a cell incubator at 37° C. for 30 minutes to form a jelly substance. 10000 endothelial cells were inoculated in each well, and the volume of the endothelial cell culture medium was 100 μL. The experiments were divided into four groups: the control group Con was only inoculated with cells without the special intervention culture; the group TNF-α: 10 ng/mL TNF-α was added to the endothelial cell culture medium and the intervention culture was performed for 18 hours; the group TNF-α+$N_{EXO}$: 10 ng/mL TNF-α together with the exosomes having a concentration of 25 μg/mL and derived from the group N in Example 4 were added to the endothelial cell culture medium, and the intervention culture was performed for 18 hours; the group TNF-α+$C_{EXO}$: 10 ng/mL TNF-α together with the exosomes having a concentration of 25 μg/mL and derived from the group C in Example 4 were added to the endothelial cell culture medium, and the intervention culture was performed for 18 hours. Each group was repeated three times.

Figure 3:
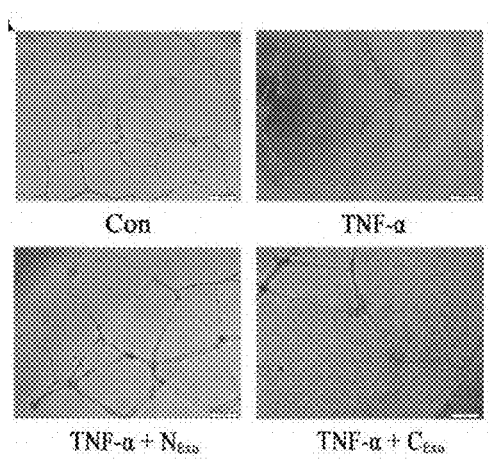
FIG. 3 is an angiogenesis diagram of the angiogenesis experiment under an inverted confocal microscope according to this disclosure.
Figure 4:
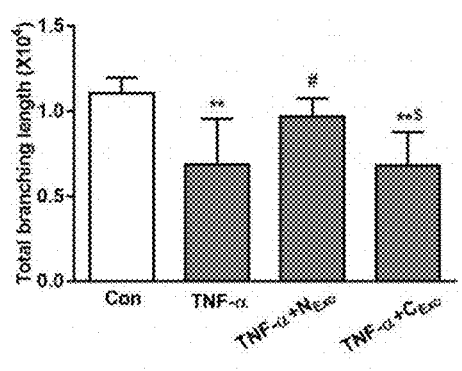
FIG. 4 is a result diagram of the total branching length of blood vessels in each view field detected by the Image J software in the angiogenesis experiment according to this disclosure.

According to the real-time observation for the angiogenesis morphology, when each of the above groups was subjected to intervention treatment for 18 hours, the angiogenesis morphology of each group reached a status for the optimum observation and quantitation. The angiogenesis condition was photographed and recorded under an inverted confocal microscope, as shown in FIG. 3, and the total branching length of each view field was measured by the Image J software as an index for evaluating the ability for angiogenesis. The results showed that, compared with the Con group, the intervention with 10 ng/mL TNF-α could significantly inhibit endothelial cell angiogenesis (P=0.002, FIG. 4). The addition of 25 μg/mL exosomes derived from the group N at the same time of TNF-α intervention could significantly improve and treat the endothelial cell vascular dysfunction caused by inflammatory factor TNF-α (P=0.037, FIG. 4), so that the angiogenesis function of the endothelial cells was restored to nearly the normal level, and there was no a statistical difference between the group TNF-α+NExo and the Con group (P=0.375, FIG. 4). The addition of the exosomes derived from the normal endothelial cell group C at the same time of TNF-α intervention had an effect similar to that of the TNF-α intervention alone, but it did not have the improvement and treatment effect for the endothelial cell angiogenesis dysfunction caused by an inflammatory factor TNF-α(P>0.05). There was a statistical difference between the group TNF-α+$C_{EXO}$ and the group TNF-α+$N_{EXO}$ group (P=0.011, FIG. 4).

The experiment results according to example 5 showed that the exosomes prepared in Example 1-Example 4 had the effect of promoting endothelial cell angiogenesis, and could be used in the manufacture of a medicament for treatment of microvascular injury, microcirculation dysfunction and cardio-cerebral infarction.

The above descriptions are preferred examples of this disclosure, but are not for limiting this disclosure. All of the changes, equivalents, modifications, and the like made within the spirit and principle of this disclosure are included in the protection scope of this disclosure.

We claim:

1. A method of preparing an exosome active formulation capable of promoting endothelial angiogenesis comprising:

(a) isolating primary umbilical vein endothelial cells
(b) culturing and passaging the primary umbilical vein endothelial cells in a first culture medium, thereby forming a culture comprising subcultured endothelial cells in a first medium;
(c) adding $1.5 \times 10^{-3}$-$1.5 \times 10^{-2}$ ng/mL anisodamine to the first medium to treat the subcultured endothelial cells;
(d) 3-5 hours after adding the anisodamime, replacing the first medium comprising anisodamine with a new endothelial cell culture medium;
(e) culturing the cells in the new endothelial cell culture medium for 18-30 hours, thereby forming a culture comprising cultivated endothelial cells in a second medium;
(f) extracting exosomes from the second medium; and
(g) identifying the exosomes.

2. The method of claim 1, wherein step (b) comprises passaging the primary umbilical vein endothelial cells 3-5 times to form the subcultured endothelial cells.

3. The method of claim 1, wherein the new endothelial cell culture medium is a basic culture medium plus 0.05 mg/mL exosome-free fetal calf serum, 0.01 mg/mL penicillin, 0.01 mg/mL streptomycin and 0.01 mg/mL endothelial growth factor.

4. The method of claim 1, wherein step (f) comprises:
(i) collecting a supernatant of the second medium;
(ii) centrifuging the supernatant of step (i) at 4° C. and 300 g for 10 minutes;
(iii) centrifuging the supernatant of step (ii) at 4° C. and 16500 g for 20 minutes;
(iv) filtering the supernatant of step (iii) through a filter membrane having a pore size of 0.2 μm;
(v) centrifuging the filtrate of step (iv) at 4° C. and 120000 g for 2 hours;
(vi) removing the supernatant of step (v); and
(vii) dissolving the solids of step (v) in a 0.01 M PBS buffer solution.

5. The method of claim 1, wherein step (g) comprises:
observing the morphology of the exosomes with a transmission electron microscope;
analyzing the particle size of the exosomes; and
quantifying the exosomal proteins.

6. An exosome active formulation for promoting endothelial cell angiogenesis produced by the method of claim 1.

* * * * *